(12) United States Patent
Xue

(10) Patent No.: US 8,229,551 B2
(45) Date of Patent: Jul. 24, 2012

(54) METHOD OF PRESENTING ELECTROCARDIOGRAPHIC DATA

(75) Inventor: Joel Q. Xue, Germantown, WI (US)

(73) Assignee: General Electric Company, Schenectady, NY (US)

( * ) Notice: Subject to any disclaimer, the term of this patent is extended or adjusted under 35 U.S.C. 154(b) by 415 days.

(21) Appl. No.: 12/624,925

(22) Filed: Nov. 24, 2009

(65) Prior Publication Data

US 2011/0125042 A1    May 26, 2011

(51) Int. Cl.
*A61B 5/0402* (2006.01)
(52) U.S. Cl. .......................... 600/509; 600/523
(58) Field of Classification Search .......... 600/509, 600/515, 516, 523
See application file for complete search history.

(56) References Cited

U.S. PATENT DOCUMENTS

| 5,803,084 | A | * | 9/1998 | Olson ........................... 600/512 |
| 7,142,907 | B2 | * | 11/2006 | Xue et al. ...................... 600/509 |
| 7,542,795 | B2 | | 6/2009 | Brodnick |
| 2006/0253044 | A1 | * | 11/2006 | Zhang et al. .................. 600/512 |
| 2012/0083706 | A1 | * | 4/2012 | Nelwan et al. ................. 600/523 |

* cited by examiner

*Primary Examiner* — Brian T Gedeon
(74) *Attorney, Agent, or Firm* — Andrus, Sceales, Starke & Sawall, LLP

(57) ABSTRACT

A system and method of presenting physiological data in a component ring. The method includes receiving a plurality of leads of physiological data. Morphology features are extracted from the plurality of leads. The morphology features are graphed by presenting a component ring associated with each of the morphology features. The system includes at least two sensors configured to collect physiological data. A processor is configured to extract amplitudes of morphology features. A graphical user interface is configured to graphically display the morphology features in a plurality of component rings.

20 Claims, 4 Drawing Sheets

METHOD OF PRESENTING ELECTROCARDIOGRAPHIC DATA

BACKGROUND OF THE INVENTION

The present disclosure relates to the field of electrocardiography. More specifically, the present disclosure relates to a method of presenting ECG component data.

An electrocardiogram (ECG) is the primary physiological measurement used for assessing the cardiac health of a patient. The ECG measures the electrical impulses propagated through the heart in a regular pattern that results in the cyclical contraction and relaxation of the heart muscle.

This electrical propagation is measured by a plurality of electrodes placed upon the patient. Based upon the number of electrodes placed upon the patient, these electrical signals may be measured at a wide variety of vectors or leads projecting out of the patient's heart in very specified directions. The most common arrangements of ECG measure either six leads or twelve leads of cardiac data.

Typically, ECG leads are analyzed by breaking the ECG data into a variety of features indicative of the depolarization and repolarization of specific anatomical locations of the heart. There are two standard types of analysis that are performed with regards to these morphological features (P wave, QRS wave, ST segment, T wave, and U wave). The timing between features within a heart beat, or between the same features of successive heart beats may be analyzed. Alternatively, or additionally, the magnitude and shape (morphology) of each of these features may be analyzed.

One difficulty with the display and interpretation of ECG data is that as more leads of ECG data are added to the analysis, thus providing a more detailed analysis of patient cardiac condition, increasingly more data must be displayed. Therefore, it is desirable to develop new methods for the efficient presentation of ECG data, particularly ECG morphology data which is often less intuitive for a clinician to interpret than temporal or duration based ECG based analysis.

BRIEF DISCLOSURE

A method of presenting electrocardiographic data includes receiving a plurality of leads of ECG data, the leads of the plurality are taken from at least one plane through the patient. Morphology features are extracted from each of the plurality of leads. A component ring is formed for each of the extracted morphology features. The component rings are representative of at least one plane through the patient. The relative amplitude and durations of each of the morphology features of each of the leads in their respective ring are graphed.

A computer readable medium is further herein disclosed that comprises computer readable code upon execution by a processor extracts morphology features from each of a plurality of electrocardiographic leads. The processor forms a spatial ring for each of the extracted morphology features. The processor indicates in the area of the spatial rings, the amplitude of the extracted morphology features in each the leads.

BRIEF DESCRIPTION OF THE DRAWINGS

The drawings illustrate the best mode presently contemplated of carrying out the invention. In the drawings.

DETAILED DISCLOSURE

Figure 1:
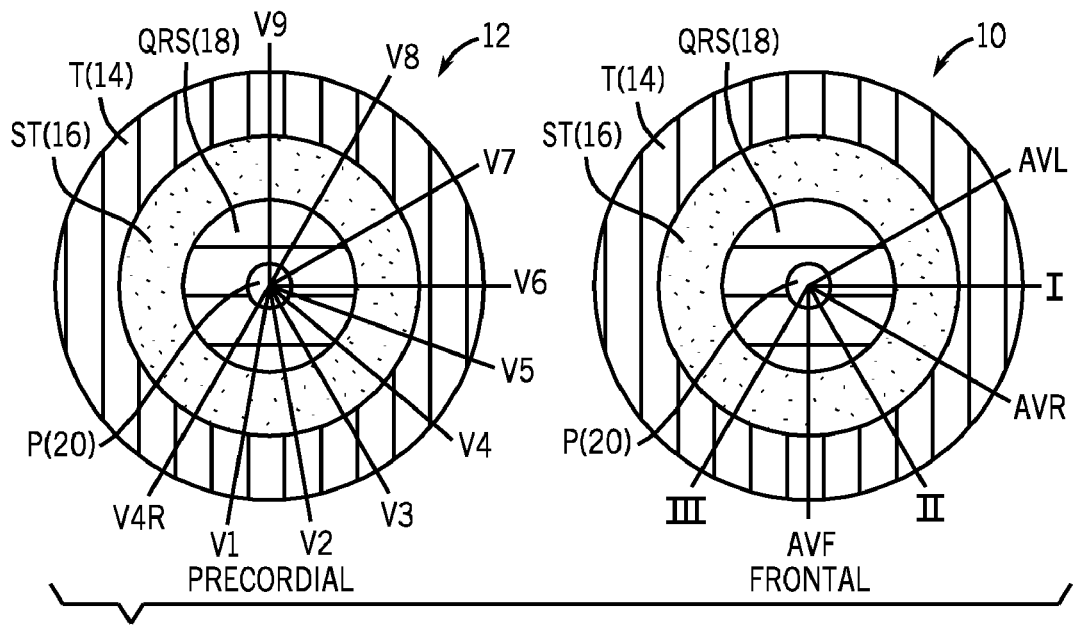
FIG. 1 depicts a exemplary frontal and precordial ECG component rings.

FIG. 1 depicts exemplary embodiments of ECG component rings developed for two different planes through the body of a patient. Frontal ECG component ring 10 and precordial ECG component ring 12. The frontal and precordial ECG component rings 10, 12 each include four component rings: the T wave component ring 14, an ST segment component ring 16, a QRS wave component ring 18, and a P wave component ring 20. In FIG. 1, the different component rings (14-20) are further distinguished from each other by using color or shading.

The frontal ECG component ring 10 also includes indications of the relative direction of each of the six predominantly frontal ECG leads. These frontal leads include leads I, II, III, AVF, AVL, and AVR. It is to be noted that lead AVR is represented in frontal ECG component ring 10 as -AVR such as to consolidate the lead representations to a single hemisphere of the frontal ECG component ring 10.

Similarly, precordial ECG component ring 12 exemplarily includes indications for ten leads commonly associated with precordial ECG measurement. These leads include, but the disclosure is not so limited, precordial leads V1-V9 as well as right precordial lead V4R.

While FIG. 1 depicts frontal ECG component ring 10 and precordial ECG component ring 12, it is to be noted that other planes through the patient may be represented with component rings, these additional planes may include, but are not limited to, a saggital plane ECG component ring. It is further to be noted that while the frontal ECG component ring 10 and the precordial ECG component ring 12 are depicted with four or five featured component rings, the representations may be made with more or fewer component rings depending upon the embodiment. In a non-limiting alternative embodiment, the frontal ECG component ring 10, the precordial ECG component ring 12 may include only three component rings, such as T wave component ring 14, ST segment component ring 16, and QRS wave component ring 18. Alternatively, embodiments may use five component rings further including a U wave component ring (not depicted) in addition to the P wave component ring 20.

Frontal ECG component ring 10 and precordial ECG component ring 12 represented in FIG. 1 may be similarly presented by a graphical display operated by a computer processor. The presentation of the frontal ECG component ring 10 and the precordial ECG component ring 12 may be achieved through the operation of the processor such as to properly control the presentation by the graphical display. Alternatively, as disclosed herein, the presented ECG component rings or ring may further form a graphical user interface (GUI) that both provides an enhanced presentation of ECG component data, but also facilitates the navigation by a clinician to additional ECG data that may be relevant to the clinician in making a determination or diagnosis.

Figure 2:
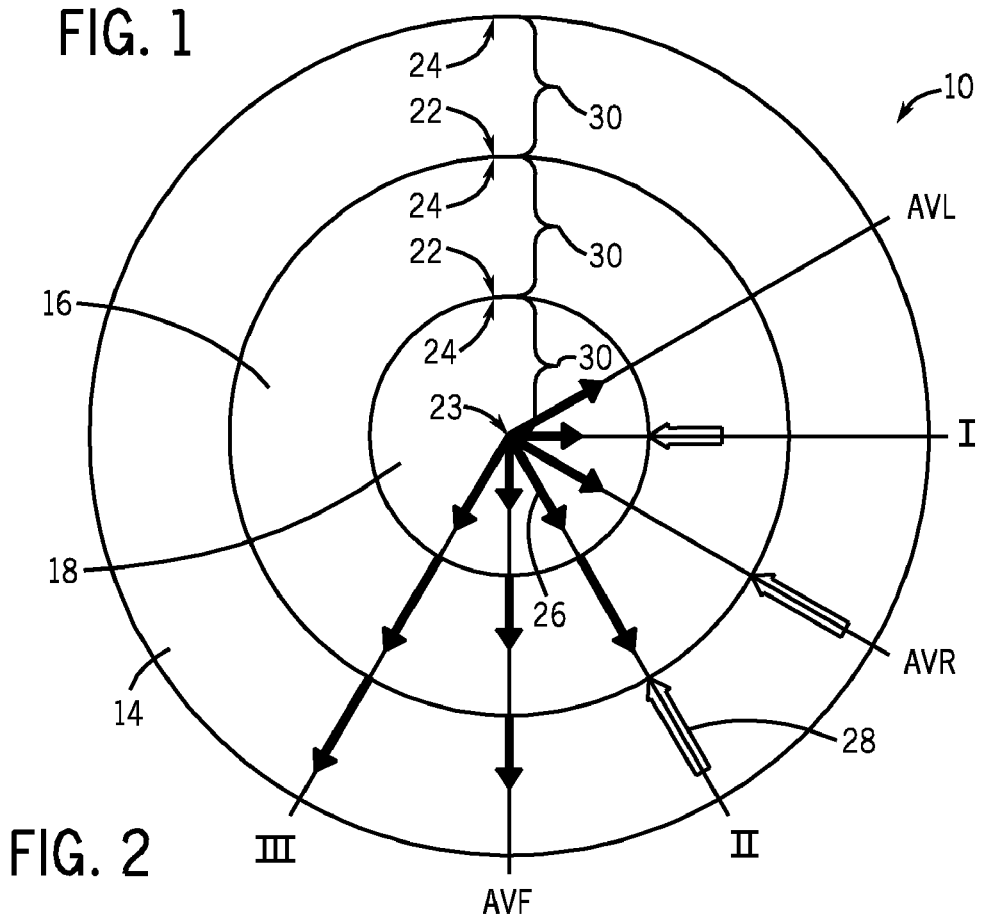
FIG. 2 depicts a more detailed embodiment of ECG data presented in frontal ECG component rings.

FIG. 2 depicts an embodiment of a frontal ECG component ring 10. This embodiment of the frontal ECG component ring 10 includes only three component rings, namely, the T wave component ring 14, the ST segment component ring 16, and the QRS wave component ring 18. It should be noted that the frontal ECG component ring 10 is depicted in FIG. 2 as a stacked plurality of spatial component rings. However, it should be noted that in alternative embodiments the individual component rings may be separated and presented as separate rings or circles that may be arranged in various spatial relationships. In some of these embodiments, the relative sizes of the component rings or circles may be the same, and the specific morphology features to which they pertain indicated by color or by labels, while in other embodiments differences in size may be used to denote the different morphology feature components presented.

The frontal ECG component ring 10 of FIG. 2 depicts an embodiment of the display of the magnitudes of the morphology features in each of the six frontal leads. Each of the component rings 14-18 embody a space. The space is defined by an inner edge 22 and an outer edge 24. If the component ring is a circle, such as QRS wave component ring 18, then instead of an inner edge 22, the component ring would have a circle center point 23. It is to be noted that in an overlap or ringed embodiment of the component rings, the outer edge 24 of an interior component ring may be the same as an inner edge 22 of the next component ring outward. The inner edges 22 of each of the component rings represent a zero or other base line value for the magnitude of each of the morphology features.

In the frontal ECG component ring 10 of FIG. 2, a plurality of vectors are depicted in relation to the inner edges 22. This plurality of vectors indicate the absolute values of the amplitudes of each of the T wave, ST segment, and QRS wave morphology features in each of the frontal ECG leads. The length of the vector extending from the inner edge 22 graphically depicts this morphology feature amplitude absolute value. The polarity of each of the morphology feature magnitudes may be indicated in a variety of ways. The frontal ECG component ring 10 of FIG. 2 represents two different ways that polarity may be indicated, and these may be used alone or in combination in embodiments. The frontal ECG component ring 10 uses color/shading with solid arrows being positive and outlined arrows being negative to indicate the polarity. The frontal ECG component ring 10 further uses the direction of the vector extending from each of the inner edges 22 to indicate the morphology feature polarity.

Thus, referring to lead II, arrow 26 is a long, solid, outwardly extending arrow that indicates a large positive magnitude for the QRS wave in lead 2. This is to be compared to arrow 28 in lead II, which is representative of the magnitude of the T wave morphology feature. Arrow 28 is indicated by an outline and it is directed inwardly. The outlined shading and inward direction of the arrow 28 indicate the negative polarity of the magnitude of the T wave morphology feature in lead 2.

The component rings (14-18) of the frontal ECG component ring 10 may be either fixedly, or dynamically scaled. In fixed scaling, the sizes of each of the component rings (14-18) remain the same size. The rings (14-18) themselves may be of different sizes compared to each other, but these sizes remain constant throughout the presentation of the morphology feature amplitude data. The fixed size of the component rings (14-18) may be determined by a preprogrammed device or institutional standard that sets the size of the component rings (14-18). These component rings may be set to be on the same scale. The height 30 of each of the rings is established based upon normal average amplitudes for each morphology feature, or normal maximum values for each morphology feature. Alternatively, the fixed height 30 of each of the component rings may be fixed to a value that is above the maximum physiological value for each of the morphology features represented by the component rings. While this embodiment may require the most dedicated GUI space in order to present the frontal ECG component rings 10, this is one embodiment that ensures that none of the presented extracted morphology feature amplitudes will exceed the fixed space dedicated to each of the morphology feature component rings.

In an alternative embodiment, the height 30 of each of the component rings 14-18 is dynamically adjusted such that the size of the component rings are continuously changing as the extracted morphology feature amplitudes are updated for presentation. Dynamically scaled embodiments of the frontal ECG component rings 10 may be continuously adjusted to have a height 30 that is equivalent to the maximum extracted morphology feature amplitude presented in each of the component rings 14-18. Alternatively, the height 30 of each of the component rings 14-18 may be adjusted to be continuously a predetermined percentage greater than the maximum extracted morphology feature amplitude. In one such embodiment, the height 30 of each of the component rings 14-18 is 25% greater than the maximum extracted morphology feature amplitude greatly presented for each particular component ring. However, this example is not intended to be limiting on the ways in which the dynamic scaling of the component ring height 30 may be achieved. In a further non-limiting example, the height 30 of each of the component rings may further be defined by a predetermined minimum height 30, below which the component rings are no longer adjusted. Such an embodiment may further include a predetermined height by which the maximum extracted morphology feature amplitude is exceeded to establish the component ring height 30.

Embodiments of the component rings using fixed or dynamically adjusting ring heights may further include indications of the current ring height. Such indications will notify any such changes to component ring weight to the clinician such that the clinician will be made aware of the new scale.

Figure 3:
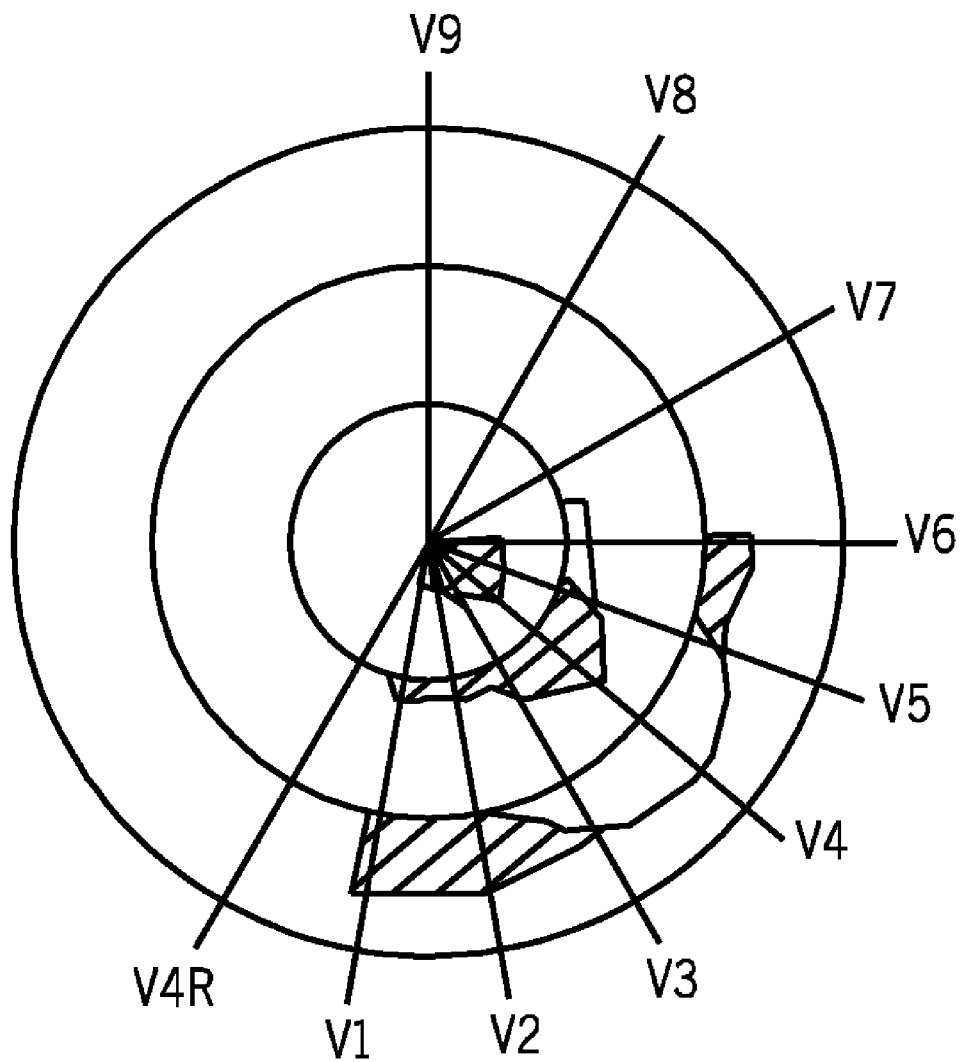
FIG. 3 depicts an alternative embodiment of ECG data presented in precordial ECG component rings.

FIG. 3 depicts precordial ECG component rings 12 that represent the electrical potentials acquired through a horizontal or precordial plane through the patient. The precordial ECG component rings 12 include the T wave component ring 14, the ST segment component ring 16, and the QRS wave component ring 18. The precordial ECG component rings 12 of FIG. 3 differ from the frontal ECG component rings 10 of FIG. 2 not only in the ECG leads that are presented, but also in how the ECG data is presented. In FIG. 3, the amplitudes of the extracted morphology features (T wave, ST segment, QRS wave) are presented in each of the associated component rings 14-18. The extracted morphology feature amplitudes are presented in the precordial ECG component rings 12 of FIG. 3 as an area, rather than as a vector as depicted in FIG. 2. In the area presentation, relationships between the extracted morphology feature amplitudes across the precordial leads may be more easily determined as the extracted amplitudes are connected to form the presented area.

This provides improved cross-lead analysis of the amplitude of the morphology features by highlighted groups of leads that exhibit similar or different amplitude characteristics. As with the arrows of FIG. 2, the amplitude areas in each of the component rings 14-18 may use color coding or shading (in a black/white or grayscale mode) such as to indicate the polarity of the extracted morphology feature amplitude. In the example of FIG. 3, shaded areas of the component rings indicate positive amplitudes and outlined areas indicate negative amplitudes. Thus, positive and/or negative amplitude for various morphology features may be easily and readily identifiable. The area between the extracted morphology feature amplitude of each of the leads may be smoothed using techniques such as averaging or spline smoothing techniques.

An alternative embodiment includes a 3-D ECG component display that presents the amplitudes of extracted morphology features from two or more planes through the body of the patient. These two or more planes may exemplarily be the frontal plane and the precordial plane; however, it may also include alternative planes, including, but not limited to, a saggital plane. The 3-D ECG component display is extrapolated from the frontal and precordial ECG leads. The area data in the frontal plane and precordial plane may be extrapolated into three-dimensional volumes using known techniques. For example, a 3-D (space) vector can be formed with X, Y, and Z axis values obtained from two orthogonal planes such as the frontal and precordial planes.

Figure 4:
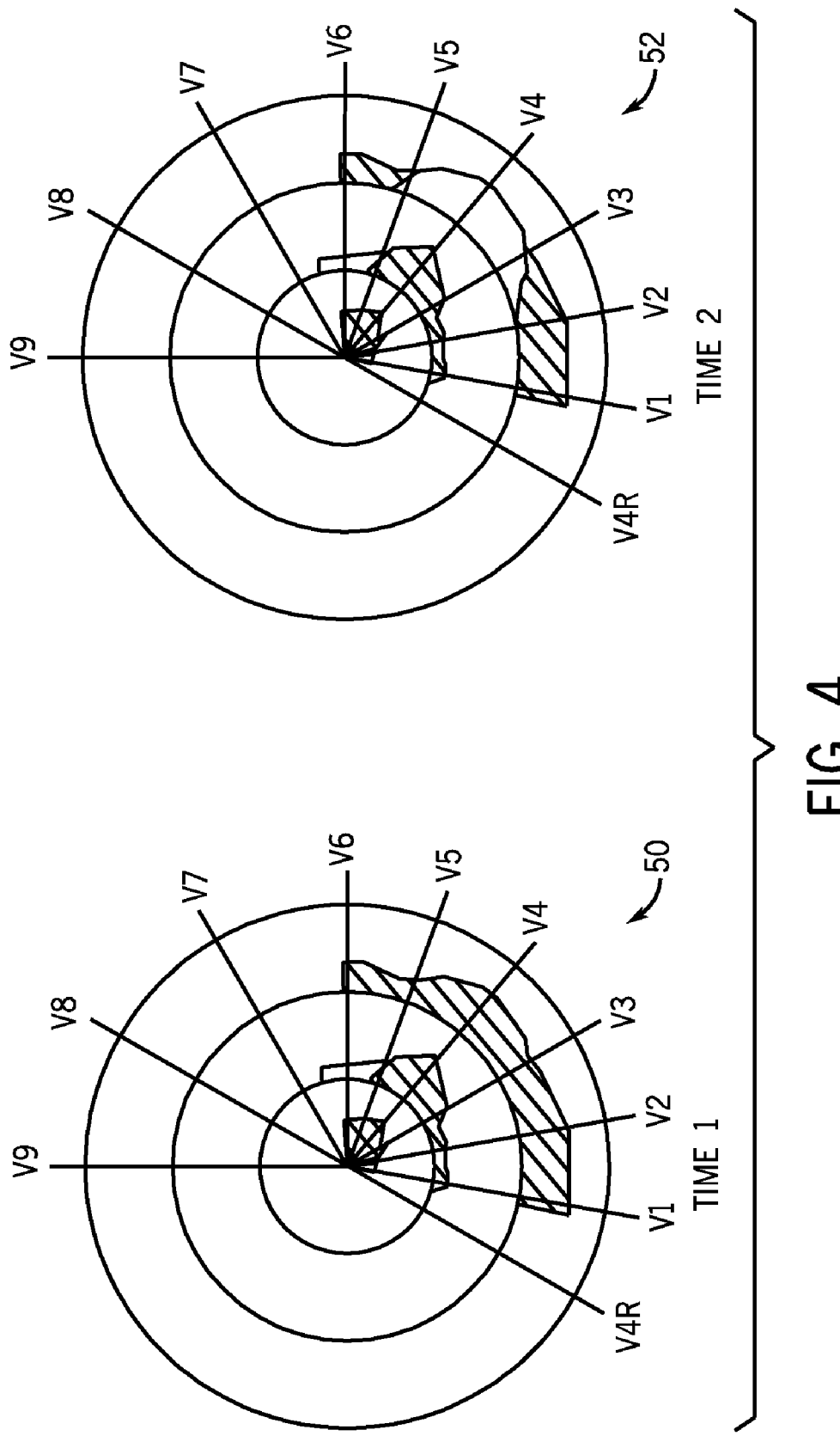
FIG. 4 depicts an embodiment of serial ECG comparison.

FIG. 4 depicts two precordial ECG component rings 50, 52. FIG. 4 depicts an example of the information presented by a graphical display during embodiments wherein the ECG component rings 50, 52 are used to facilitate serial ECG comparison. Precordial ECG component ring 50 and precordial ECG component ring 52 both represent morphology feature amplitudes obtained from the precordial leads of an ECG obtained from a patient. The precordial ECG component ring 50 presents stored historical ECG data, while the precordial ECG component ring 52 represents currently, or recently collected ECG data. Previous applications of serial ECG comparison required the clinician to look at specific waveforms for each of the leads of ECG data and attempt to draw comparisons between the plurality of leads in the historical and the recently or currently acquired ECG data. This can be difficult for a clinician to readily identify these differences when a large plurality of leads must be compared (6-18+). However, in the ECG component rings 50, 52 of FIG. 4, the graphical indications of the amplitudes of the most important morphology features are readily determined and the major differences between the morphology feature amplitudes in the two sets of data become apparent. Thus, from a quick visual inspection between the precordial ECG component ring 50 and the precordial ECG component ring 52, a reviewing clinician can see that the amplitudes of all of the S-T durations across views V1-V6 have increased during the time. Additionally, the inversion of the T wave across leads V3, V4, and V5 is also readily apparent.

In an alternative, not depicted embodiment, rather than a side-by-side serial comparison as presented in FIG. 4 with precordial ECG component ring 50 and precordial ECG component ring 52, a single composite ECG component ring may be formed that rather than displaying the amplitude of the extracted morphology features in each of the leads, display the differences in the extracted morphology feature amplitudes between the two sets of ECG data. Thus, in this alternative embodiment, the ECG component ring displays the result of the serial analysis of the ECG data across all of the leads in the displayed plane. The displayed results will thus graphically present the areas of difference between the collected sets of ECG data.

The graphical representation of amplitude and polarity of morphology features that the reviewing clinician is already accustomed to interpreting by virtue of the presentation of the previously disclosed embodiments, would similarly be applicable to the presentation of this derived serial comparison data. For the same reasons as discussed previously, the ECG component ring quickly identifies and highlights those areas where the recently or currently acquired ECG data differs from the control historical, or previously acquired data. This promotes efficiency of ECG data review by the reviewing clinician as a large amount of numeral and graphical ECG data across a plurality of precordial leads is presented in a single graphical presentation, highlighting the areas of most interest to the reviewing clinician.

Figure 5:
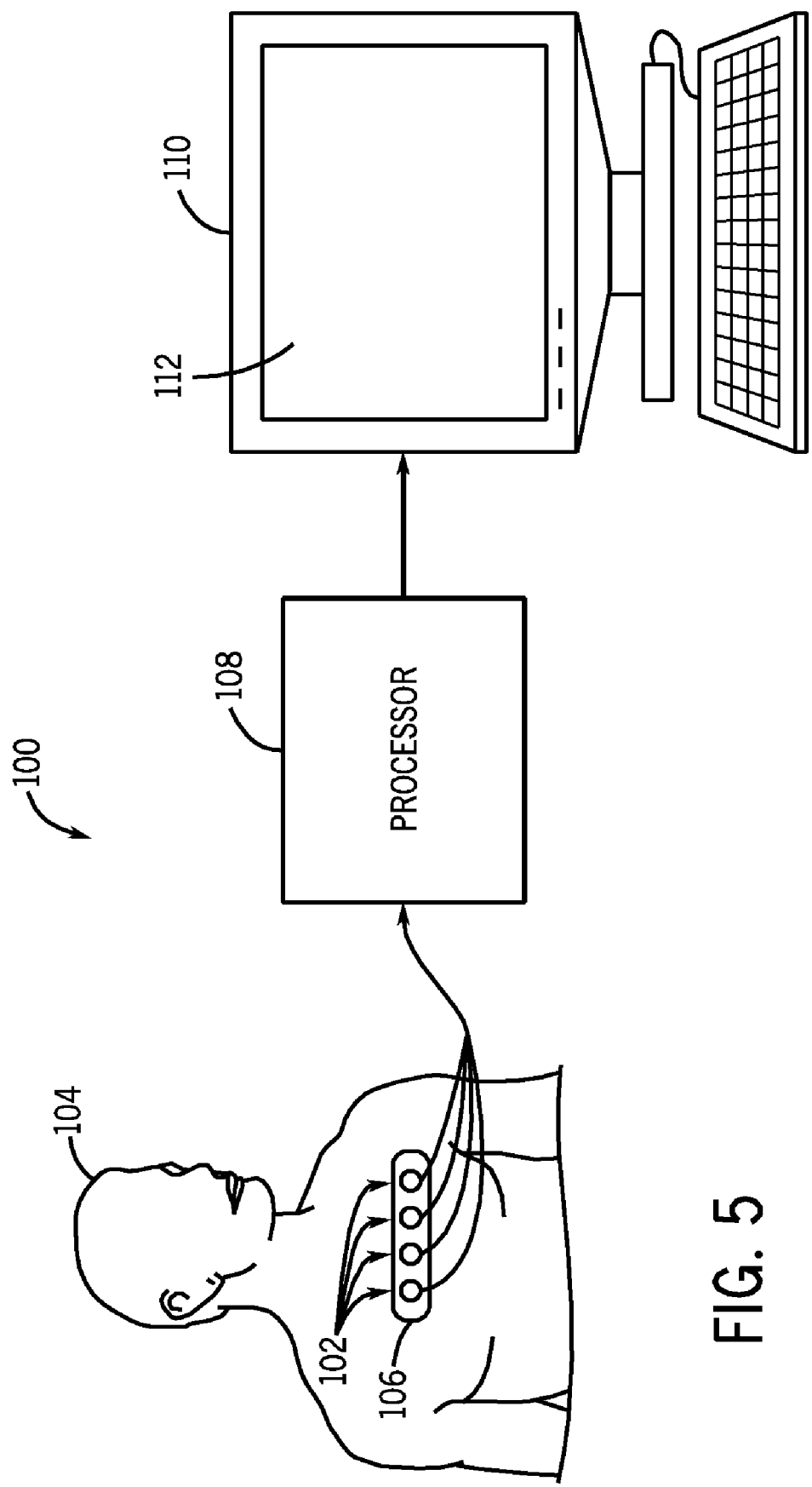
FIG. 5 is a system diagram of a system for presenting physiological data.

FIG. 5 is a display system 100 that in an embodiment presents ECG data using the ECG component rings as disclosed herein. The display system 100 includes a plurality of sensors 102 attached to a patient 104. The sensors 102 may be constructed in an assembly such as a sensor array 106 for attachment to the patient 104. The sensor of array 106 may be configured to properly place the electrodes 102 in the proper orientation in placement across the patient 104 in order to obtain the desired leads of ECG data. These leads of ECG data may be precordial leads or frontal leads, or any other combination of ECG leads thereof.

The sensors 102 provide the collected physiological data to a processor 108. The processor 108 is communicatively coupled to a computer readable medium that is programmed with computer readable code such as to operate the processor in a manner where the processor is able to extract a plurality of morphology features from each of the leads of physiological data obtained by the sensors 102. The morphology features extracted from the ECG data in the present disclosure may include, but is not limited to or requires, P wave, QRS wave, ST segment, T wave, and U wave. The processor 108 further identifies the amplitude of each of the extracted morphology features including the polarity of the amplitude.

The processor 108 provides the extracted morphology feature amplitude to workstation 110. The workstation 110 includes audio and visual presentation devices, such as a graphical display and speaker. The workstation 110 further includes user input devices that may include, but are not limited to, keyboard, a mouse, or a touch screen. The workstation 110 under the direction of the processor 108 presents a graphical user interface 112 on the graphical display of the workstation 110. The graphical user interface 112 presents the extracted morphology feature amplitudes in the form of the ECG component rings as disclosed herein. The graphical user interface 112 may present the extracted morphology feature amplitudes in any of the embodiments depicted in FIGS. 1-4.

As an additional feature of the graphical user interface 112, the clinician can use the displayed ECG component rings in order to navigate the stored physiological data in order to be presented with more detailed and specific ECG data. In these embodiments, the clinician may select any of the ECG component rings in order to access the numerical or ECG wave form data associated with the morphology feature of the selected component ring.

In an example, the clinician may quickly navigate to view the numerical values and ECG waveforms for the T waves across all of the displayed leads simply by selecting the T wave component ring 14 from FIGS. 1-4 with a user input device of the workstation 110. Additionally, the clinician may similarly use the ECG component rings displayed on the graphical user interface 112 to navigate to numeral or waveform data for a specific presented ECG lead that may be of particular interest to the clinician. The clinician accesses this more detailed data through the graphical user interface 112 by selecting a lead identifier as seen in connection with FIGS. 1-4. The selection of one of these lead identifiers will navigate the clinician to the numeral and waveform ECG data associated with that particular lead. This additional data may be presented in a new or a pop-up window presented by the workstation 110, or may navigate away from the displayed ECG component ring to an alternative presentation with numeral and waveform ECG data.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of presenting physiological data, the method comprising:
   receiving a plurality of leads of physiological data, the leads taken with a plurality of sensors from at least one plane through a patient;
   extracting morphology features from each of the plurality of leads; and
   graphing the morphology features from each of the plurality of leads on a graphical user interface by presenting a component ring with a ring height associated with each of the morphology features and graphing each of the extracted morphology features in each of the plurality of leads in the associated component ring.

2. The method of claim 1, wherein the physiological data is electrocardiographic (ECG) data and the morphology features are an amplitude and duration of each of the P wave, QRS wave, ST segment, and T wave.

3. The method of claim 2, wherein the morphology features further include an amplitude and duration of the U wave.

4. The method of claim 1, further comprising dynamically modifying the height of each of the component rings to be the highest absolute value of the amplitude of the morphology features of each ring.

5. The method of claim 1, wherein the physiological data is ECG data and the at least one plane is a frontal plane and the plurality of leads are I, II, III, aVR, aVL, and aVF.

6. The method of claim 1, wherein the physiological data is ECG data and the at least one plane is a horizontal plane and the plurality of leads comprises at least V1, V2, V3, V4, V5, and V6.

7. The method of claim 1, wherein the at least one plane is a three-dimensional sphere.

8. The method of claim 7, wherein the three-dimensional sphere is extrapolated from leads in the frontal plane and the horizontal plane.

9. The method of claim 1, further comprising:
   indicating areas wherein the amplitude of a morphology feature is positive; and
   indicating areas wherein the amplitude of a morphology feature is negative.

10. The method of claim 9, wherein the absolute value of the amplitude of the morphology feature is presented in the component rings and the polarity of the amplitude is visually indicated.

11. The method of claim 9, wherein the indicating steps are performed using arrows within the component rings.

12. A computer readable medium comprising computer readable code embodying a computer program that upon execution by a processor performs the steps of:
   extracting morphology features for each of a plurality of electrocardiographic (ECG) leads;
   forming a first plurality of component rings on a graphical user interface, each component ring in the plurality being associated with one of the extracted morphology features, each component ring having an area and representing an amplitude of the associated morphology feature with respect to each of the leads;
   indicating in the associated component ring, the amplitudes of each of the morphology features extracted from each of the ECG leads.

13. The computer readable medium of claim 12, further comprising presenting the component rings and the ECG leads in a configuration representative of at least a plane through a patient.

14. The computer readable medium of claim 12, further comprising:
   forming a second plurality of component rings similar to the first plurality of spatial rings; and
   indicating in the associated rings of the second plurality of component rings, amplitudes of morphology features extracted from a plurality of historical ECG leads.

15. The computer readable medium of claim 14, further comprising:
   performing a comparative analysis between the amplitudes of the morphology features indicated in the first plurality of component rings and the amplitudes of the morphology features indicated in the second plurality of component rings.

16. A system for displaying physiological data, the system comprising:
   at least two sensors configured to collect physiological data from a patient, wherein the physiological data is a plurality of leads of physiological data obtained in a plane through the patient;
   a processor configured to extract amplitudes of morphology features from each of the plurality of leads of physiological data; and
   a graphical user interface configured to graphically display the extracted amplitudes of morphology features of the plurality of leads, wherein the graphical user interface presents a plurality of component rings, each component ring of the plurality being associated with one of the morphology features of the plurality of leads, the graphical user interface graphs the extracted amplitudes from each of the plurality of leads in the component ring associated with the extracted morphology feature.

17. The system of claim 16 wherein the graphical user interface further comprises a plurality of navigation buttons, each navigation button of the plurality associated with one of the plurality of leads of physiological data and selection of one of the plurality of navigation buttons causes the presentation of the collected physiological data of the selected lead.

18. The system of claim 16 wherein each component ring of the plurality of spatial rings has a height and the graphical user interface dynamically adjusts the height of each of the plurality of component rings to be the maximum absolute value of the morphology feature amplitudes presented in the component ring.

19. The system of claim 16 wherein the graphical user interface further graphs extracted morphology feature amplitudes from a plurality of leads of historical physiological data in the plurality of component rings.

20. The system of claim 19, wherein the graphical user interface further graphs in the plurality of component rings, a difference between the extracted morphology feature amplitudes from the plurality of leads of collected physiological data and the extracted morphology feature amplitudes from the plurality of leads of historical physiological data.

* * * * *